United States Patent
Adams et al.

(10) Patent No.: US 6,441,396 B1
(45) Date of Patent: Aug. 27, 2002

(54) IN-LINE ELECTRICAL MONITOR FOR MEASURING MECHANICAL STRESS AT THE DEVICE LEVEL ON A SEMICONDUCTOR WAFER

(75) Inventors: Edward D. Adams, Richmond, VT (US); Arne W. Ballantine, Round Lake, NY (US); Richard S. Kontra; Alain Loiseau, both of Williston, VT (US); James A. Slinkman, Montpelier, VT (US)

(73) Assignee: International Business Machines Corporation, Armonk, NY (US)

( * ) Notice: Subject to any disclaimer, the term of this patent is extended or adjusted under 35 U.S.C. 154(b) by 22 days.

(21) Appl. No.: 09/695,038

(22) Filed: Oct. 24, 2000

(51) Int. Cl.[7] .................................................. H01L 23/58
(52) U.S. Cl. ........................................ 257/48; 257/51
(58) Field of Search ............................. 438/14, 17, 18; 257/48, 49, 51; 324/209

(56) References Cited

U.S. PATENT DOCUMENTS

| | | |
|---|---|---|
| 4,125,820 A | 11/1978 | Marshall |
| 4,144,493 A * | 3/1979 | Lee et al. .................... 324/765 |
| 6,265,729 B1 * | 7/2001 | Nelson et al. ................. 257/48 |
| 6,291,834 B1 * | 9/2001 | Hasegawa ..................... 257/48 |
| 6,339,229 B1 * | 1/2002 | Shiga et al. ................... 257/48 |

FOREIGN PATENT DOCUMENTS

JP 406349919 A * 12/1994

OTHER PUBLICATIONS

IBM Technical Disclosure Bulletin, vol. 34, No. 12, May 1992, On–Chip Electromigration Sensor Using Silicon Device, pp. 197–198.

* cited by examiner

Primary Examiner—Olik Chaudhuri
Assistant Examiner—Hoai Pham
(74) Attorney, Agent, or Firm—Schmeiser, Olsen & Watts; Howard J. Walter, Jr.

(57) ABSTRACT

A method is presented for measuring and monitoring the mechanical stress at the device level which occurs intrinsically during the fabrication process or which is induced via extrinsic means. The method applies the fact that the current-voltage (I-V) characteristics of a diode change as the diode is subjected to mechanical stress. The method is applicable to monitoring stress at the microscopic and device levels at various stages in the semiconductor wafer fabrication process. Apparatus for implementing the method is also presented.

18 Claims, 15 Drawing Sheets

IN-LINE ELECTRICAL MONITOR FOR MEASURING MECHANICAL STRESS AT THE DEVICE LEVEL ON A SEMICONDUCTOR WAFER

BACKGROUND OF THE INVENTION

1. Technical Field

The present invention relates generally to the field of semiconductor device formation, and more specifically to a method and apparatus, integrated with said devices, for measuring mechanical stress induced in those devices. Such stress is either induced by the intrinsic fabrication process of the devices, or by extrinsic means, such as a vacuum chuck used during electrical tests. The method is particularly useful for measuring mechanical stress on semiconductor devices induced by the process of formation of either dielectric-filled isolation trenches or by semi-recessed oxide (SROX) isolation regions, which abut the devices of interest. The process of forming such isolation regions is well known in the art to be a significant source of stress.

2. Related Art

Dielectric-filled trench isolation is a common method of electrically isolating solid state silicon devices. It is especially common in complementary metal-oxide semiconductor ("CMOS") technology as an alternative to back-biased isolation diffusion techniques used in negative-channel metal-oxide semiconductor ("NMOS"), positive-channel metal-oxide semiconductor ("PMOS"), or bipolar technologies. However, dielectric-filled trench isolation is difficult to implement in CMOS technology.

There are two significant drawbacks to the use of dielectric-filled trench isolation. First, the oxidation of the etched trench, which induces generally compressive stresses into the laterally adjacent silicon. Second, there is a densification of the dielectric that is deposited to fill the trench, and this densification induces tensile stress into the adjacent silicon. Thus, at the conclusion of the isolation trench construction process, the stress induced in the silicon is both compressive close to the surface, and tensile deeper down. These resulting stresses effect both device defects and device parameters.

Certain aspects of trench isolation as used in semiconductor structures causes the semiconductor structure to behave much the same as a piezoresistive device (i.e., a device whose resistance changes with the applied stress), and the effects of induced mechanical stress can modulate the nominal electrical behavior of a properly designed device, or array of such devices, for the purpose of measuring the induced stress. It is to be noted that extrinsically generated stress will also modulate device behavior and that this stress, too, can effectively be measured.

Devices known in the related art are designed to measure stress under controlled conditions, and are not meant to measure the process-induced stresses which are an accidental by-product of very large-scale integration ("VLSI") fabrication.

Therefore, it would be most useful to be able to monitor stress during semiconductor device fabrication with the aim of modifying processes so as to reduce, or at least control, the stress and its resultant effects.

SUMMARY OF THE INVENTION

The invention disclosed herein presents a method and related structures that enable monitoring of stress acting upon a semiconductor structure. A method and apparatus for measuring the stress at microscopic levels is disclosed. The invention relies on the dimensional dependence between the width of a device and the inherent resistivity in the device.

The present invention discloses a method and apparatus used to measure the stress at a sub-chip (i.e., device and chip) level with resolution of stress effects on electrical conduction. The present invention permits obtaining data on the position dependence of stress effects on devices, including orientational effects on a semiconductor wafer or substrate used in production of VLSI devices and circuits. The present invention also allows monitoring of the dependence of stress on device size, particularly via wide-to-narrow diode behavior.

The present invention provides a structure for measuring stress in a semiconductor device comprising: a pn diode formed on the surface of a semiconductor device, said diode being bounded by a first shallow trench isolation region having predetermined dimensions; a diffusion region formed on the surface of the wafer, said diffusion region being bound by a second shallow trench isolation region having the same dimensions as the first shallow trench region; and contacts formed on said diode and diffusion region for passing current through the diode and through said diffusion region.

The present invention additionally provides a method of monitoring stress in a silicon substrate comprising the steps of: forming a first device comprising a pn diode in a first n-well region of a p-well formed in said silicon substrate, said pn diode having a geometry defined by a dielectric-filled trench; forming a second device comprising a p-type diffusion region in a second n-well region formed in said p-well region of said silicon substrate, said second n-well region having a geometry substantially the same as the geometry of said first n-well region and defined by a dielectric-filled trench; subtracting a first current measurement through said second device from a first current measurement from said first device.

The present invention further provides a method of using a stress monitor structure formed in a semiconductor wafer comprising the steps of: applying a current to the stress monitor structure; measuring a resultant bias voltage induced in the stress monitor structure by the current; comparing the stress-induced resultant bias voltage to a reference non-stress-induced bias voltage; and determining the amount of stress-induced electrical parameter variations in the semiconductor wafer.

The present invention also provides a stress monitoring unit comprising: a semiconductor material forming a base structure, said base structure containing a diode structure and a non-diode structure; said diode structure formed in the semiconductor material; said non-diode structure including a plurality of isolation trenches surrounding the diode structure, said isolation trenches being filled with a dielectric material; a system for applying an electrical potential across the diode structure, thereby inducing a diode current to flow through the diode structure; a system for measuring the diode current; and a system for translating the amount of diode current measured into dimensional units representing the stress on the base structure.

The present invention also discloses a stress monitoring set comprising: at least one pair of diode devices, or an array or plurality of diode devices, said pair consisting of a first device and a second device, wherein said first device is a reference device, and said second device (or array of secondary devices) is (are) a measurement device.

The present invention additionally discloses a stress monitoring system for monitoring mechanical stress in a semiconductor substrate containing trench isolation regions comprising: a semiconductor material forming a base structure, said base structure containing a diode structure and a non-diode structure; said diode structure formed in the semiconductor material; said non-diode structure including a plurality of isolation trenches surrounding the diode structure, said isolation trenches being filled with a dielectric material; a system for applying an electrical potential across the diode structure, thereby inducing a diode current to flow through the diode structure; a system for measuring the diode current; and a system for translating the amount of diode current measured into dimensional units representing the stress on the base structure.

BRIEF DESCRIPTION OF THE DRAWINGS

For an understanding of the nature and advantages of the present invention, reference should be made to the following detailed description taken in connection with the accompanying drawings wherein.

DETAILED DESCRIPTION OF THE INVENTION

The invention utilizes a semiconductor structure upon which is located a diode which is surrounded by an isolation trench. The process of forming an isolation trench is well-known in the art. The isolation trench is filled with dielectric, typically an oxide or nitride. The resulting structure can be employed as a device for monitoring mechanical stress acting upon the semiconductor structure at the location of the diode. The trench isolation causes the semiconductor structure to behave much the same as a piezoresistive device, in that the effects of induced mechanical stress can modulate the nominal electrical behavior of a properly designed device, or array of such devices, for the purpose of measuring the induced stress. Extrinsically generated stress will also modulate device behavior and this stress, too, can effectively be measured. The end result is a stress monitor that measures stresses on a microscopic level, rather than only at the coarser device level.

There exist three types of stress which are of concern during semiconductor device fabrication. These are surface tensile stress, compressive trench stress, and shear stress.

The surface tensile stress is primarily caused by the combination of the trench fill and the surface passivation films, such as silicon oxides and nitrides, which can cause dislocations and gate oxide defects. Surface tensile stress can retard or enhance oxide growth, which can in turn increase "bird's-beaking" in some manufacturing processes.

The term "bird's beak" refers to a structural feature produced as a result of the lifting of the edges of the nitride layer during subsequent oxidation steps. Compressive trench stress can result in corner device turn-on, and anomalous PFET behavior.

In a related application, deep trench capacitors, which share similar fabrication processes to trench isolation, also have similar stress-related problems, namely those due to shear stress causing dislocations, and compressive stress causing spurious electron-hole pair generation.

Observed stress-induced device parametric changes include bandgap effects of carrier density, which varies exponentially, and changes in mobility, which varies linearly; saturation current ("$I_d$") which can be enhanced or retarded up to about 7%; and reduced boron out-diffusion in positive-channel field effect transistor ("PFET") source/drains ("S/D"), which directly affects the electrical channel length, $L_{eff}$.

Figure 1:
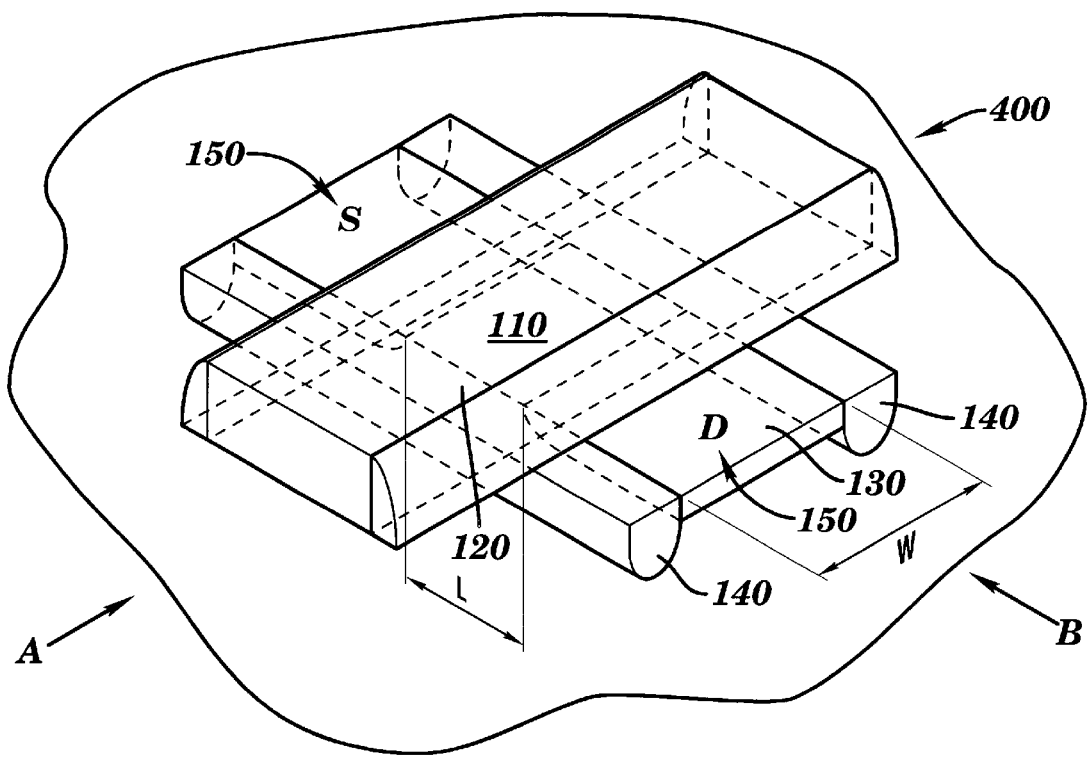
FIG. 1 illustrates a typical FET in perspective showing channel length, L, and channel width, W.

Stress effects become very important as device dimensions shrink. FIG. 1 is a perspective view of a wafer portion 100, containing a typical field effect transistor ("FET") device, showing the channel 110 of channel length ("L") 120 and the channel width ("W") 130. Trench isolation 140 is shown along the length of the device 110. Trench isolation 140 exists (but is not shown) at the extrema along the width of the device 110 as well, where it forms the outer border of the S/D diffusions 150. Two perspectives are indicated, A and B.

Figure 2:
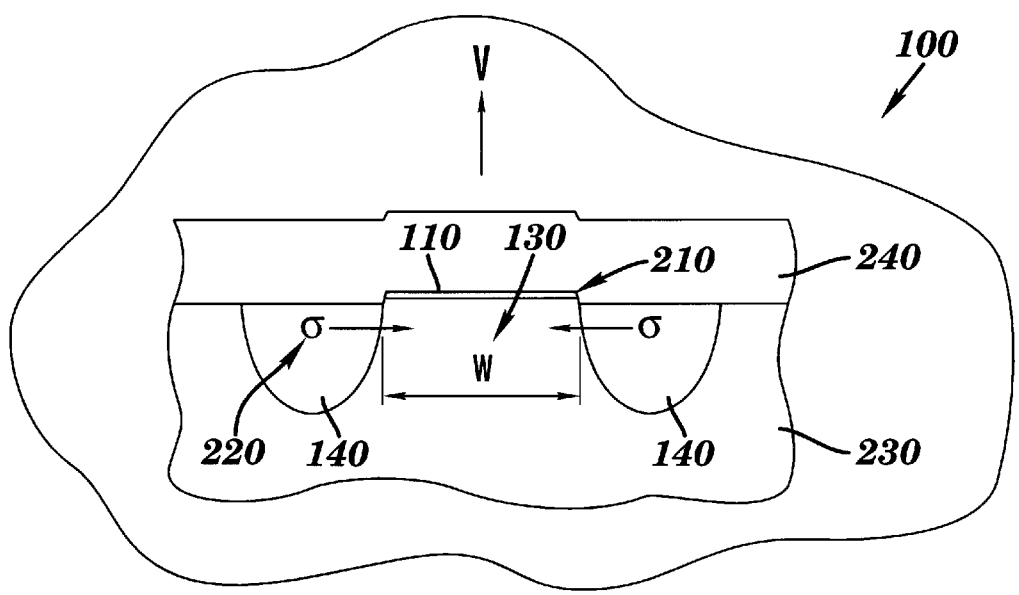
FIG. 2 is a cross-section view of the typical FET of FIG. 1 through the gate/channel region parallel to the device width.

FIG. 2 is a cross-sectional view of the typical FET device 110, viewed at perspective B in FIG. 1, as constructed in a substrate 230 and capped with a polysilicon layer 240, through the gate/channel region 210 parallel to the channel width 130. The symbol "σ" 220 is used to indicate stress. In the channel length direction, stress affects mobility ("$\mu$"), the effective electrical channel length ("$L_{eff}$"), and the drain-to-source current at maximum drain bias ("$I_{dsat}$"), In the device width direction ("W"), stress affects the threshold voltage ("$V_t$"), the effective electrical channel width ("$W_{eff}$"), the mobility ("$\mu$"), and to second order, $L_{eff}$ In the vertical direction ("V"), the stress affects $V_t$ and $I_{dsat}$, and to some extent, $\mu$. Generally, as W decreases, σ increases in magnitude. In the present case, the strong modulation of the minority carrier density by stress can be advantageously used to monitor process-induced stress due to reductions in channel width W.

Figure 3:
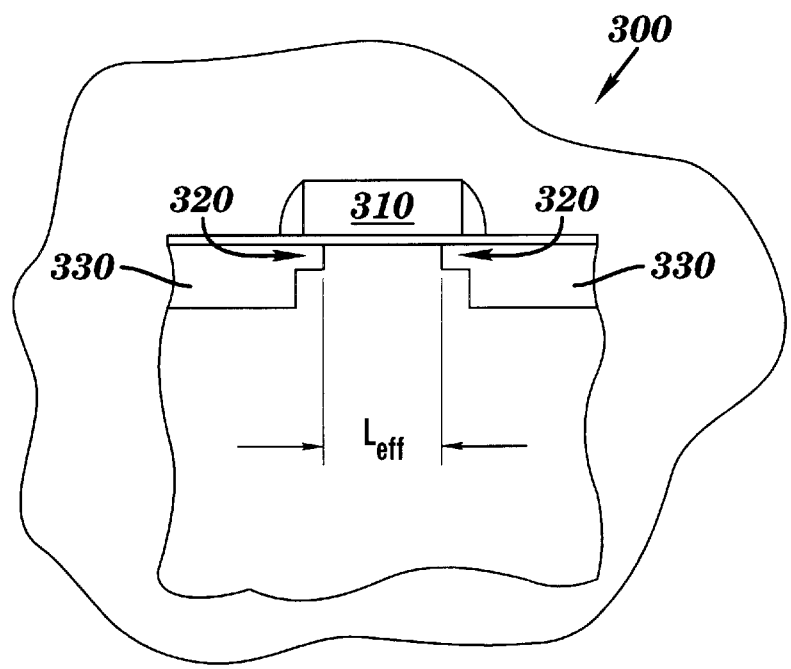
FIG. 3 is a cross-section view of the typical FET of FIG. 1 through the channel region, taken in the channel length direction.

FIG. 3 is a cross-sectional view along perspective A in FIG. 1 of a portion of a semiconductor substrate 300 containing a typical device 310, through the channel region (in the channel length direction), showing where $L_{\it eff}$ is measured. Note that this measurement excludes the S/D extension regions 320, and the S/D diffusion regions 330.

Figure 4:
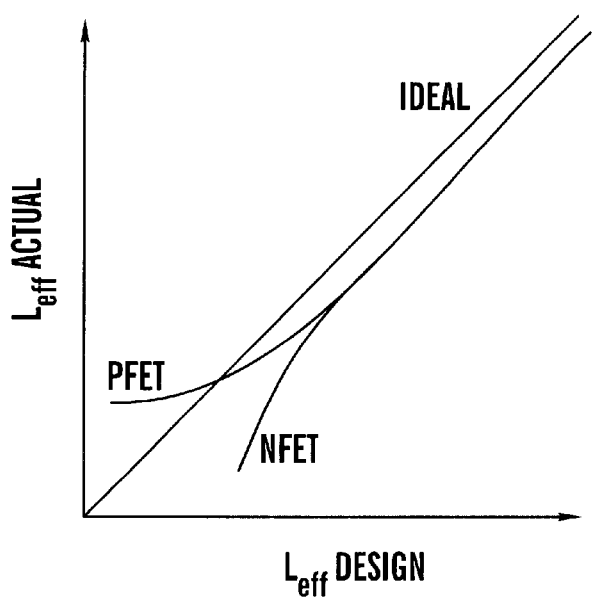
FIG. 4 is a graph representing the deviation of actual, measured, effective electrical channel length for an FET versus the design channel length.

FIG. 4 is a graph representing the deviation of actual, measured, effective electrical channel length ($L_{\it eff}$) for an FET versus the design channel length ($L_{design}$) The graph presents data for three devices, namely, an ideal device, an NFET device, and a PFET device. The ideal relationship is equality, which is the straight-line relationship in the graph. Note that there is a significant departure from the ideal curve as $L_{\it eff}$ becomes smaller. Generally, the effective channel length, $L_{\it eff}$, is less than the design length, $L_{design}$, and therefore its trend generally lies below the ideal curve, except as shown at very small channel lengths, where the PFET trends above the ideal, the NFET farther below. These excessive, small channel length deviations are due to a variety of physical effects, one of which is mechanical stress.

Figure 5:
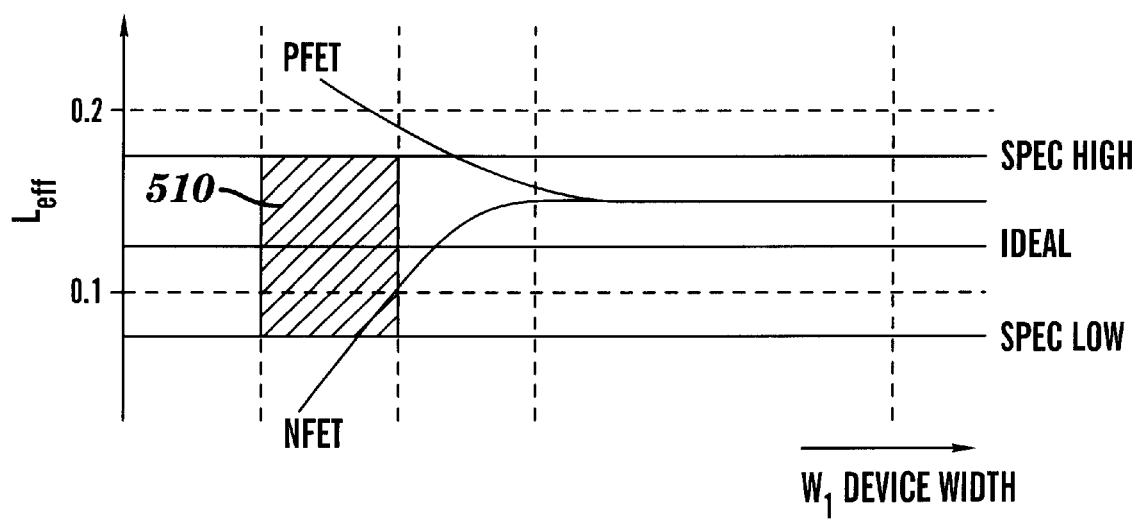
FIG. 5 is a graph representing the dependence of FET effective electrical channel length on the device width, $W_d$.

FIG. 5 is a graph representing the dependence of FET effective, electrical channel length, $L_{\it eff}$, on the device width, $W_d$, for the ideal device, an NFET device, and a PFET device. For large $W_d$ (moving to the right along the horizontal axis) the design and electrical channel lengths are nearly equal. This is represented by the horizontal line labeled "Ideal". As $W_d$ is reduced the effective channel length for both NFET and PFET can be drastically affected by the increasing mechanical stress due to the closer proximity of the isolation regions, and eventually exceed design specifications as shown.

For very small devices (e.g. , where $L_{design}$<0.2 μm) $L_{\it eff}$ rolls-off as a function of W for the NFET, but rolls-up for the PFET. This poses a problem, since the cross-hatched area 510 of FIG. 5 represents the region wherein the maximum performance of the device should be obtained. Significant contributors to the $L_{\it eff}$ roll-off/roll-up phenomena include both stress modulating the bandgap, and/or stress modulating the dopant lateral diffusion as discussed by T. Hook, et al. The following references are hereby incorporated by reference: T. B. Hook, S. Biesemanns, and J. Slinkman, "The dependence of channel length on channel width in narrow-channel CMOS Devices for 0.350–0.13 μm technologies.", IEEE Elect. Dev. Lett., Feb. 21, 2000, pp85–87; and H. Park, "Point-defect based modeling of dislocation loops and stress effects on dopant diffusion in silicon," PhD Thesis, Univ. Of Florida, 1993.

The present invention takes advantage of the strong dependence of the minority carrier density on mechanical stress in order to measure its effects on the electrical devices described above. The method of the present invention describes both a diode structure and a non-diode, reference structure. The reference structure is necessary to reduce or entirely factor out the effects of parasitic devices in the diode structure itself. First, a theory of operation of a diode structure under varying states of stress is described, then the embodiment of the diode and reference structures are described in detail.

Diode current is measured in either forward or reverse bias volts ("V"). Only the forward bias case is discussed herein. The relationship of measured net diode current, $I_d(V,\sigma,W)$ due to stress induced by two isolation trenches spaced a distance ("W") apart is expressed by equation (1):

$$I_d(V,\sigma,W;V_{well})=I_d(V,\sigma=0; W)\cdot e^{\sigma\cdot\delta\Omega/kT}-I_r(V_{well,\ \sigma},W) \quad (1)$$

where the mechanically unstressed diode current is $$I_d(V,\sigma=0, W)=I_0\cdot(e^{qV/kT}-1) \quad (2)$$

and where $I_r$ is the reference device current, σ is hydrostatic stress, δΩ is the stress activation volume of silicon (i.e., on the order of $10^{-22}$ cm$^3$), k is Boltzmann's constant (1.38× $10^{-23}$ J/K (joules/kelvin)), and T is the temperature (°K).

Both the diode and reference devices embodied by this invention require an $N_{well}$ diffusion which forms a junction with a p+ diffusion. This junction forms a parasitic diode, the characteristics of which need to be accounted for in extracting the dependence of diode current on mechanical stress.

For the reference device, $V_{well}$ is the p+ to $N_{well}$ bias. The reference device is described in detail infra. The exponential dependence of $I_d$ with stress is due to the change in bandgap induced by stress, thus strongly modulating the local minority carrier density. $I_0$ is the standard pre-factor which depends upon carrier diffusion length. It is a weak, linear function of mechanical stress and can be approximated by its zero stress value. The reference device current, $I_r(V_{well},\sigma, W)$, has a voltage and stress dependence similar to that of $I_d$, as shown by equation (3):

$$I_r(V_{well},\sigma,W)=I_0\cdot(e^{qV_{well}/kT}-1)\cdot e^{qV_{well}/kT} \quad (3)$$

Figure 6A:
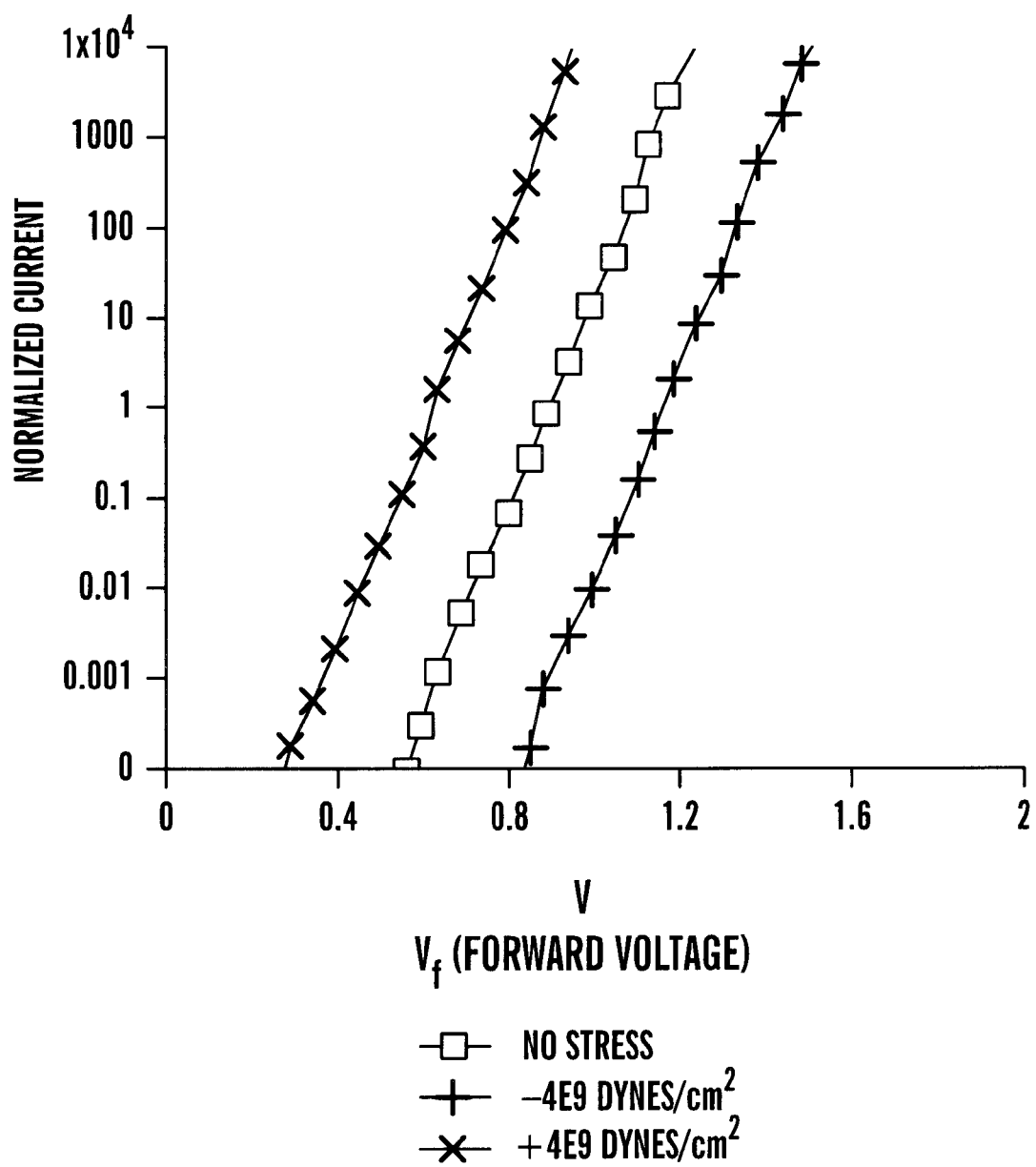
FIG. 6A is a graph showing the dependence of the lateral n+/p+ diode current as a function of forward diode bias voltage ("$V_f$") at different stress states.

The $N_{well}$ voltage ("$V_{well}$") can be tuned independently of V for optimal sensitivity. However, in principle, for zeroing out the effects of the parasitic diode, $V_{well}$ should be set equal to the bias voltage V. FIG. 6A shows the dependence of the lateral n+/p+ diode current as a function of forward diode bias voltage, $V_f$, at different stress states. The stress values used are typical of that exerted by the isolation region on a device due to the fabrication process. The current values are normalized to the value at 1.0 V. The stress is given in dynes/cm$^2$. The values of stress shown, +/−4.0×10$^9$ dynes/cm$^2$, are near the allowable limit, i.e., near the critical shear stress, 1.0×10$^{10}$ dynes/cm$^2$, of the silicon substrate, at which stress value a dislocation will occur. A positive stress value (e.g., +4.0×10$^9$ dynes/cm$^2$) indicates tensile stress, while a negative stress value (e.g., −4.0×10$^9$ dynes/cm$^2$) indicates compressive stress.

Figure 6B:
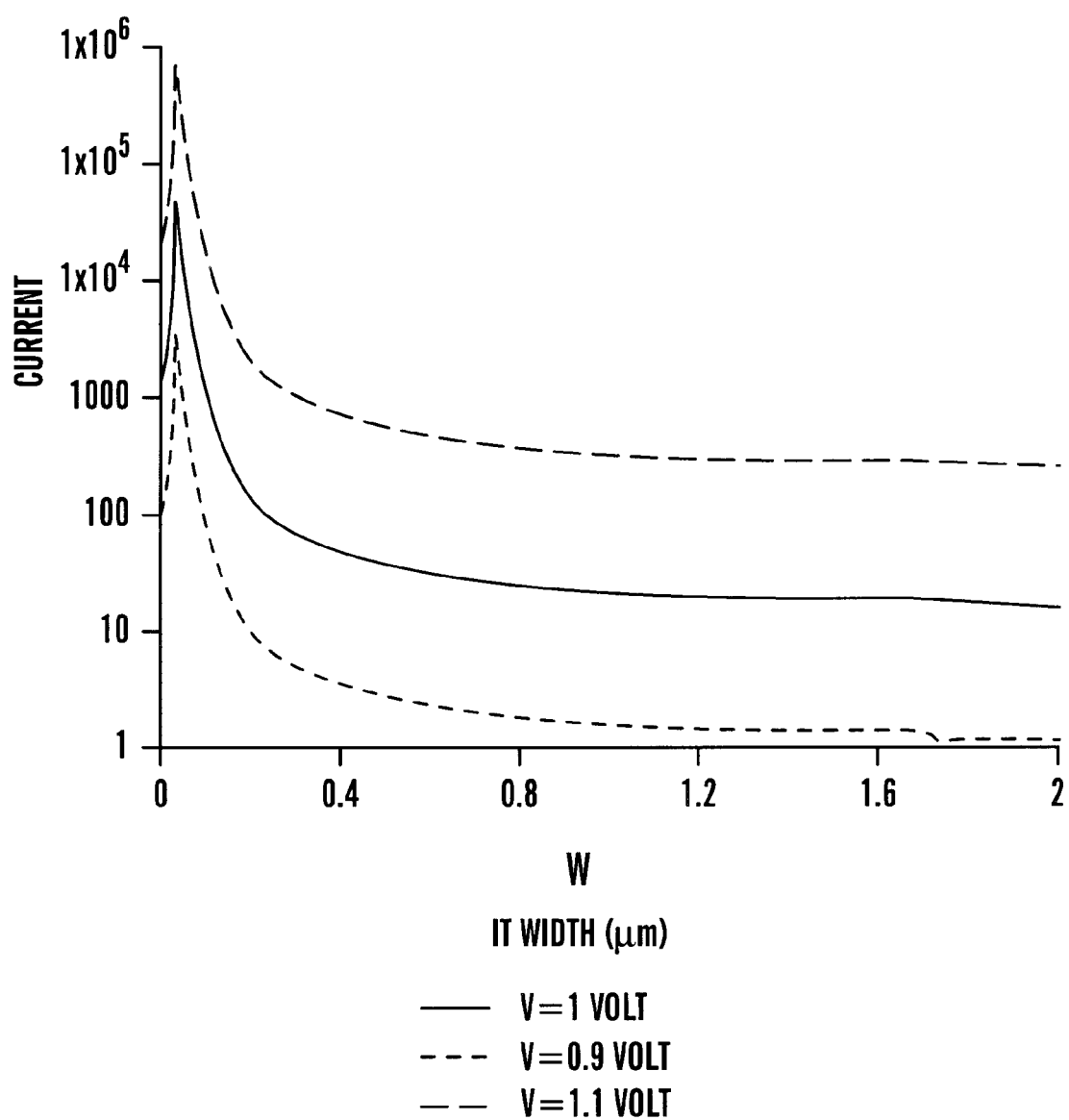
FIG. 6B is a graph showing the calculation of the diode stress as a function of isolation trench spacing ("W").

FIG. 6B is a calculation of the diode stress as a function of the isolation trench spacing, W, which shows that stress can substantially modulate the magnitude of the diode current.

Figure 6C:
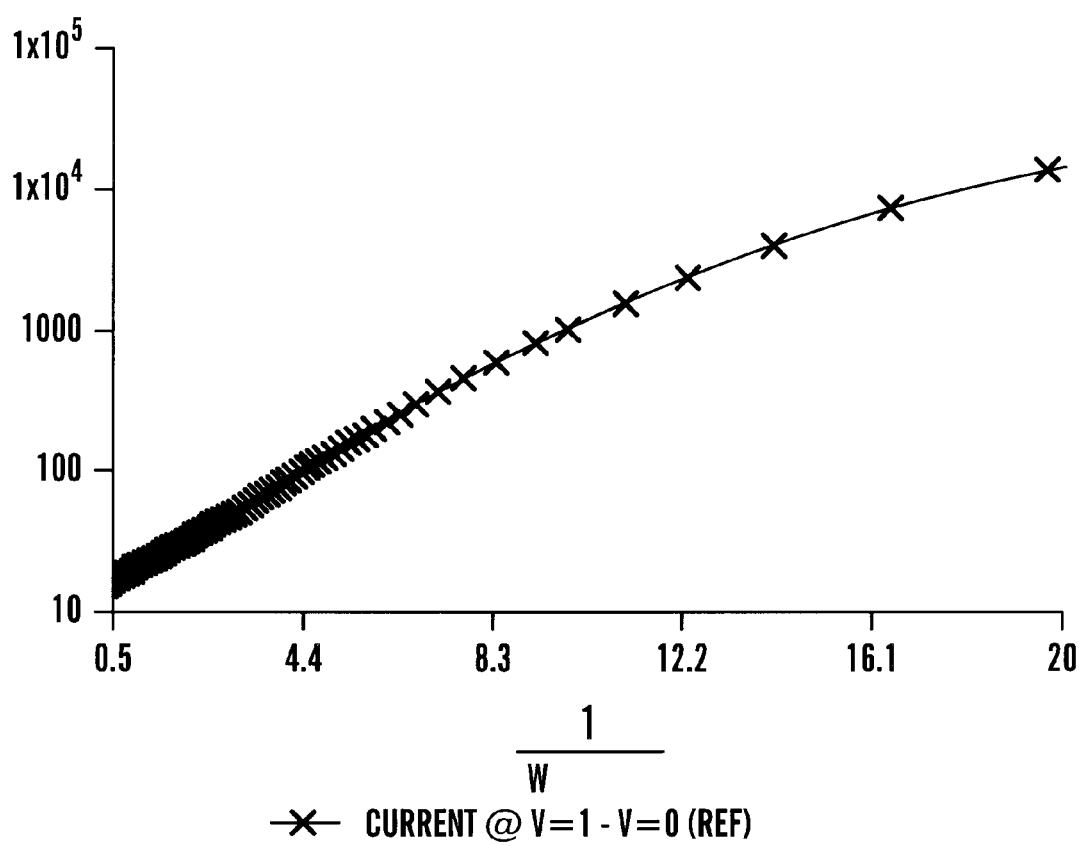
FIG. 6C is a graph showing the diode current difference relative to reference as a function of inverse trench spacing ("1/W").

Finally, FIG. 6C is a plot of the diode current difference relative to the reference device as a function of inverse trench spacing (1/W). Clearly, the signal grows as the trench spacing shrinks, making the disclosed measurement device a sensitive detector of mechanical stress. The acquired signal, for example, can therefore be used to set a limit to the maximum allowable induced stress by calibration to previously determined $L_{\it eff}$ values for specific NFET/PFET characterizations.

By correlation to In-Line-Test $L_{\it eff}$ data, the mechanical stress data can be used to discriminate the effects of stress on device behavior from other process-induced variations, such as PC linewidth variations, spacer oxide thickness variations, and extension dopant implant variations.

Figure 7A:
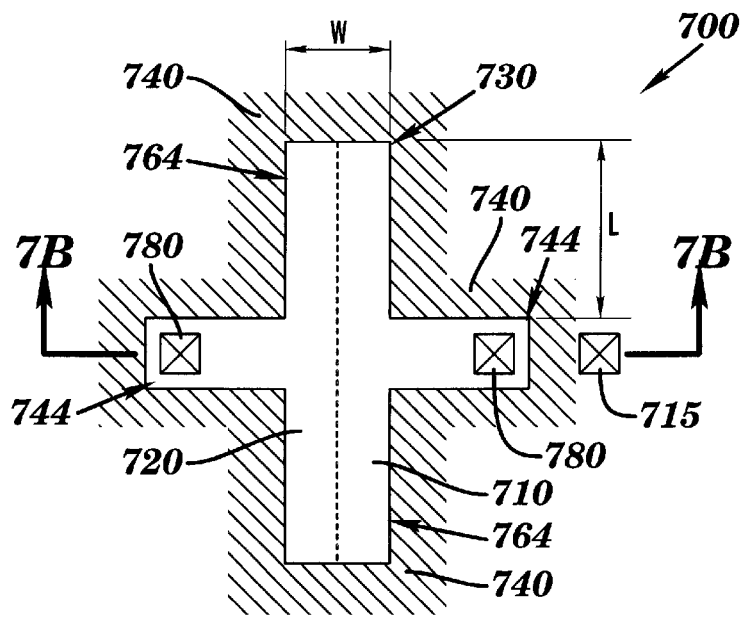
FIG. 7A is a plan view of the measurement device of the present invention.
Figure 7B:
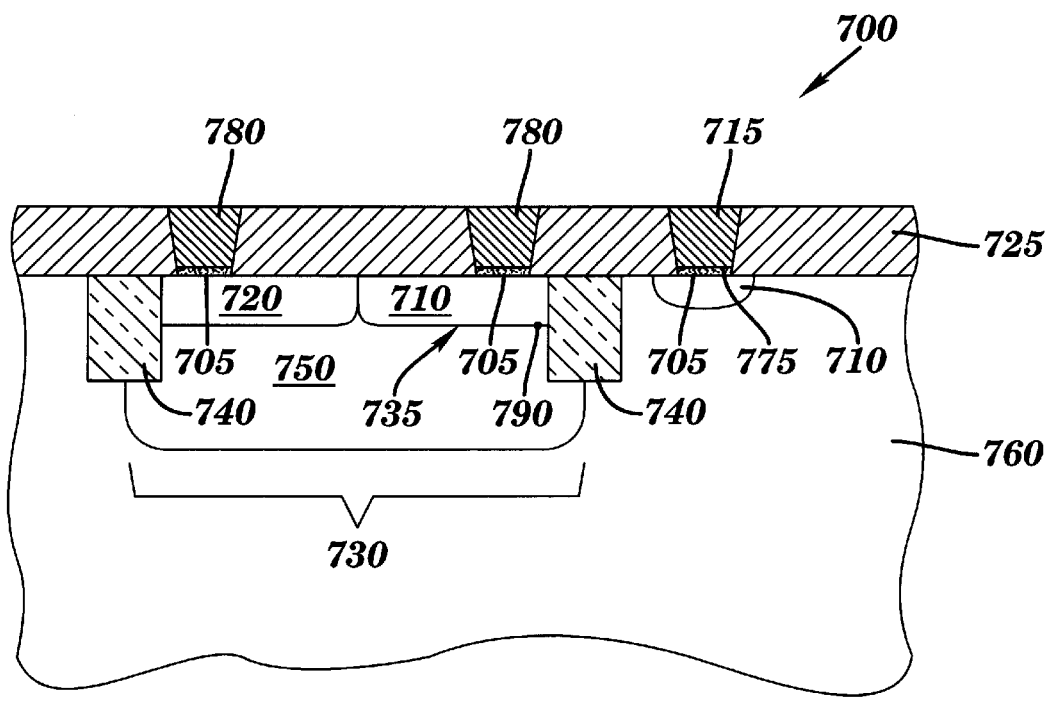
FIG. 7B is a cross-sectional side view of the measurement device taken at line 7B—7B of FIG. 7A.

FIG. 7A is a plan view of the measurement device 700 of the present invention. (The fabrication process by which the measurement device 700 is formed is described infra in the discussion of FIGS. 12A through 12E.) FIG. 7B is a cross-sectional side view of the measurement device 700 taken at line 7B—7B of FIG. 7A. It shows that the measurement device 700 comprises both p-type 710 and n-type 720 diffusions (thus forming a pn diode 730). The pn diode 730 is surrounded by trench isolation 740 in an n-well 750, and this n-well 750 is in turn located in a p-well 760. Electrical contacts 780 to the p-type and n-type diffusions 710, 720 and a p-well contact 715 are provided. A parasitic diode 790 is located at the p-type diffusion 710 and n-well junction 735. The measurement device 700 is substantially cross-shaped, that is, having pairs of arms extending at right angles from each other, for two reasons. The "horizontal" arms 744, having length L and width W, provide locations for the contacts spaced away from the n-well junction 735. The "vertical" arms 764 provide for increased n-well junction 735 length which amplifies the desired effect and minimizes processes variations. The entire surface of the substrate, excluding electrical contact areas, is covered by a layer of dielectric material 725. A layer of silicide 705 underlies the electrical contact 715, 780 areas.

Figure 8A:
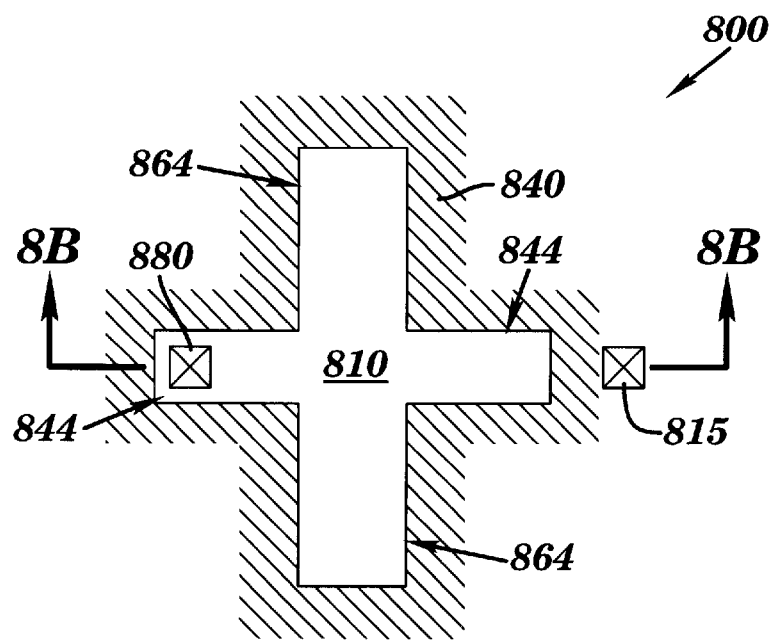
FIG. 8A is a plan view of the reference device of the present invention.
Figure 8B:
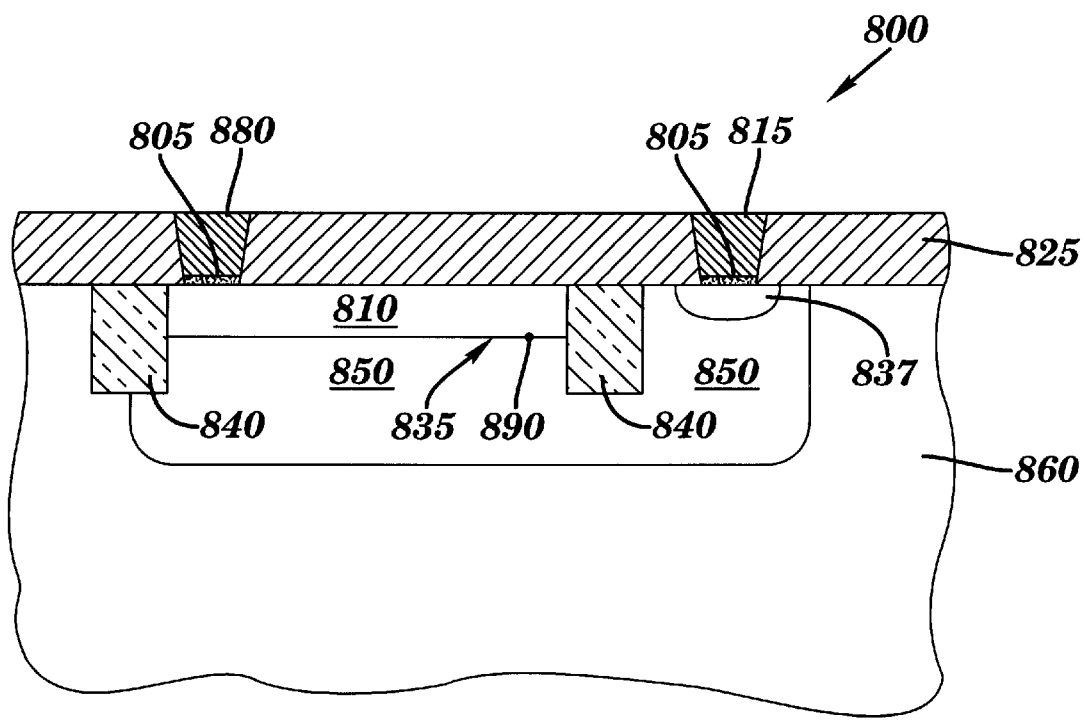
FIG. 8B is a cross-sectional side view of the reference device taken at line 8B—8B of FIG. 8A.

FIG. 8A is a plan view of the reference device 800 of the present invention. FIG. 8B is a cross-sectional side view of the reference device 800 taken at line 8B—8B of FIG. 8A. It can be seen that the reference device 800 comprises a p-type diffusion 810 surrounded by trench isolation 840 in an n-well 850, which in turn is located in a p-well 860. An n-type diffusion 837 also permits electrical contact access to n-well 850. Electrical contacts 880 to the p-diffusion 810, and a contact 815 to the p-well, are provided. Thus, a parasitic vertical diode 890 is located at the p-type diffusion 810 and the n-well junction 835. The horizontal arms 844 and the vertical arms 864 of the reference device 800 are essentially identical in length and width to those of the measurement device 700 (FIGS. 7A, 7B). The entire surface of the substrate, excluding electrical contact areas, is covered by a layer of dielectric material 825. A layer of silicide 805 underlies the electrical contact 815, 880 areas.

Figure 9:
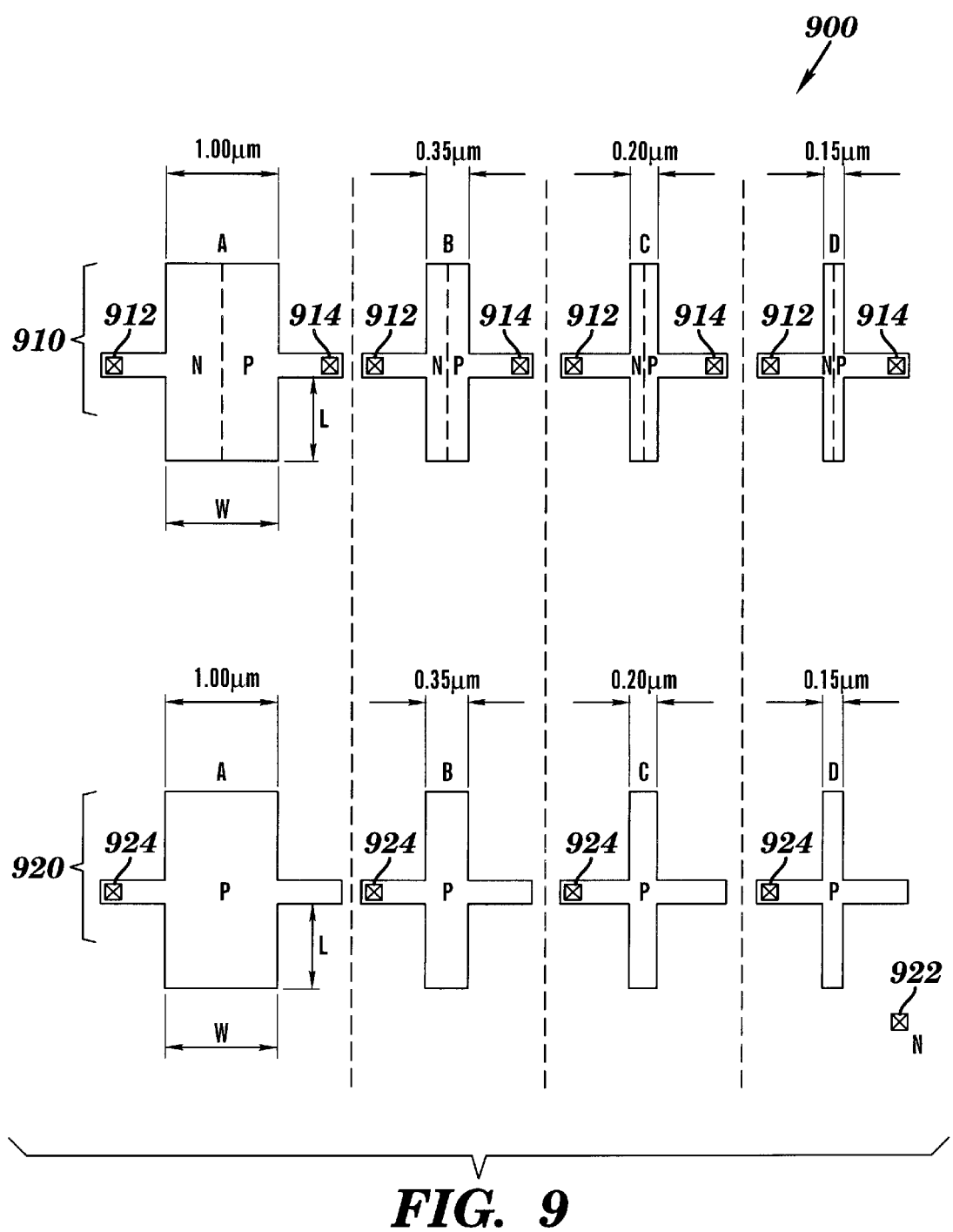
FIG. 9 depicts a monitor set comprised of four pairs of measurement and reference devices of the present invention.

FIG. 9 depicts a stress monitor set 900 comprised of pairs (A, B, C, D) of measurement devices 910 and reference devices 920. These device pairs 910, 920 differ only in the changes in their width ("W") from one pair to another; all pairs 910, 920 have the same length ("L"). The differences in device width ("W") are useful to modulate the stress.

Figure 10:
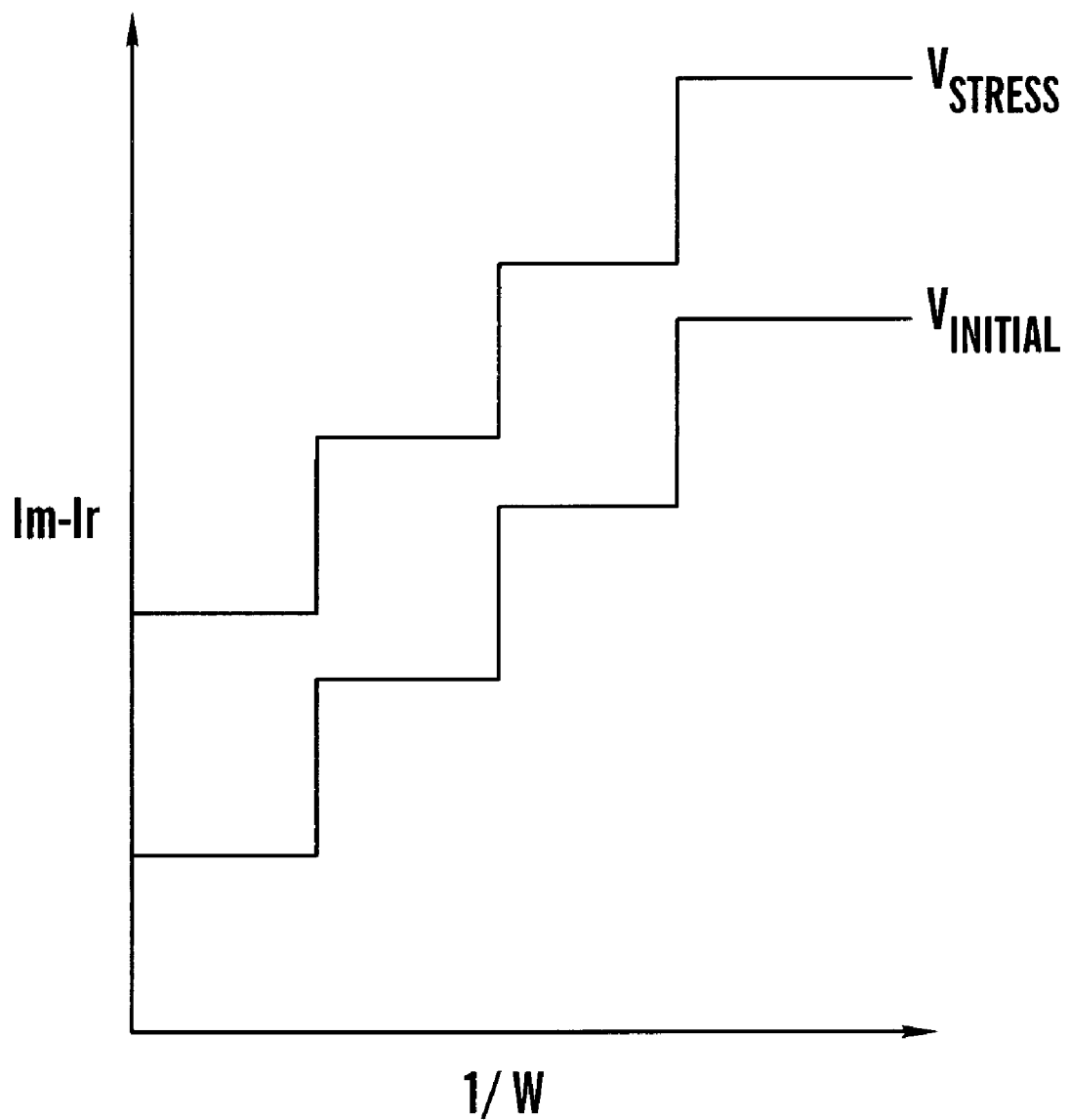
FIG. 10 is a graph of data resulting from probing of the monitor set of the present invention.

FIG. 10 is a graph of typical data taken from the monitor set 900 via application of test probes at: n-well contacts 912 for the measurement devices 910; 922 for the reference devices 920; p-well contacts 914 for the measurement devices 910; and 924 for the reference devices 920. Note that the monitor set 900 could be probed repeatedly throughout wafer fabrication, from contact formation through completion of the wafer by bringing the contacts up through all the wiring levels. In FIG. 10, $I_m$ is the current measured in the diode structure and $I_r$ is the current in the reference device. The current differential $(I_m-I_r)$ vs. 1/W is plotted, and can be compared to FIG. 6C. In FIG. 10, the first measurement curve labeled $V_{initial}$ is obtained early in wafer fabrication. A subsequent curve, $V_{stress}$, is measured later in the wafer fabrication process. If the stress has increased, the $V_{stress}$ measurement will have a greater current differential $(I_m-I_r)$ than the initial measurement. The difference between $V_{initial}$ and $V_{stress}$ indicates size sensitivity to stress.

Figure 11:
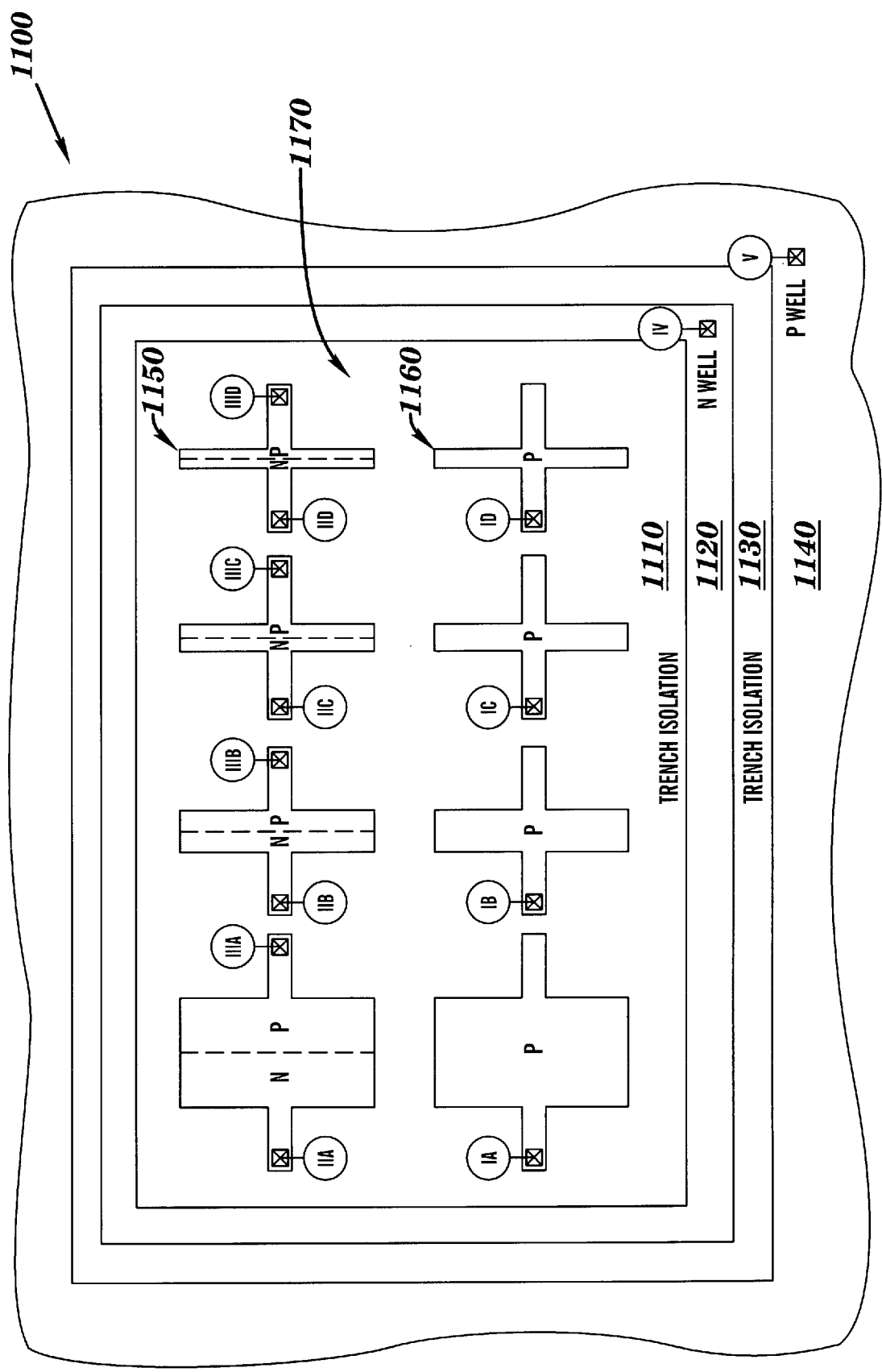
FIG. 11 is a plan view of a self-contained monitor device according to the present invention.

FIG. 11 is a plan view of a self-contained monitor device 1100 according to the present invention. The monitor set 1100 is comprised of pairs of measurement devices 1150 and reference devices 1160. These device pairs 1150, 1160 are surrounded by trench isolation 1110, and are formed in an n-well 1120. The n-well 1120 is itself bounded by a second trench isolation 1130, and formed in a p-well 1140. Table 1, infra, indicates voltage levels for various contacts (e.g., I, II, III, IV, V) as indicated in FIG. 11.

TABLE 1

| Contact | Voltage Level |
| --- | --- |
| I | biased at 0 to +2 v |
| II | ground (0 V) |
| III | biased at 0 to +2 v |
| IV | ground (0 V) |
| V | ground (0 V)* |

*Alternatively, a −1 V back bias can be applied to p-well contact V to minimize substrate leakage; this may be necessary to implement the invention in future devices.

Figure 12A:
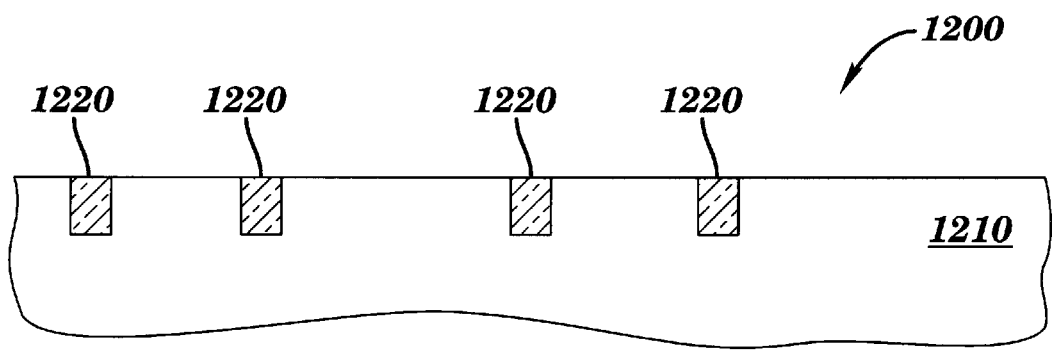
FIGS. 12A through 12E show cross-sectional views illustrating the fabrication of a diode measurement and reference device pair according to the present invention.
Figure 12B:
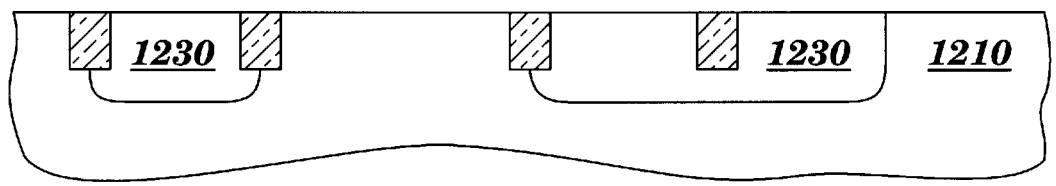
Figure 12C:
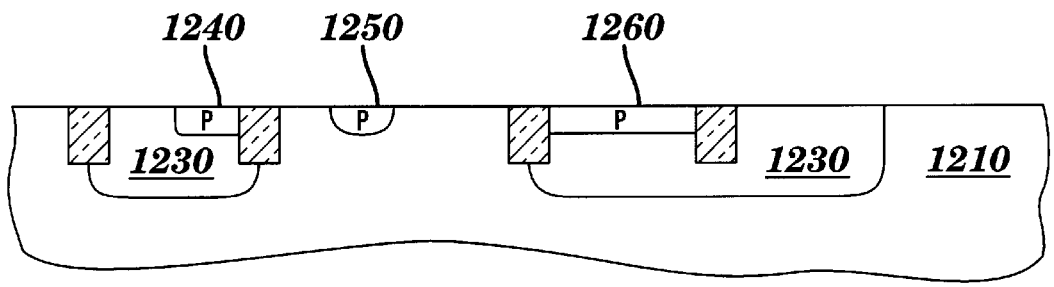
Figure 12D:
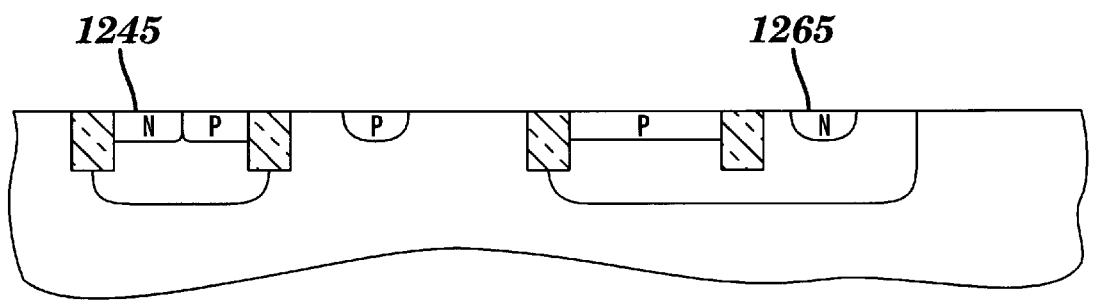
Figure 12E:
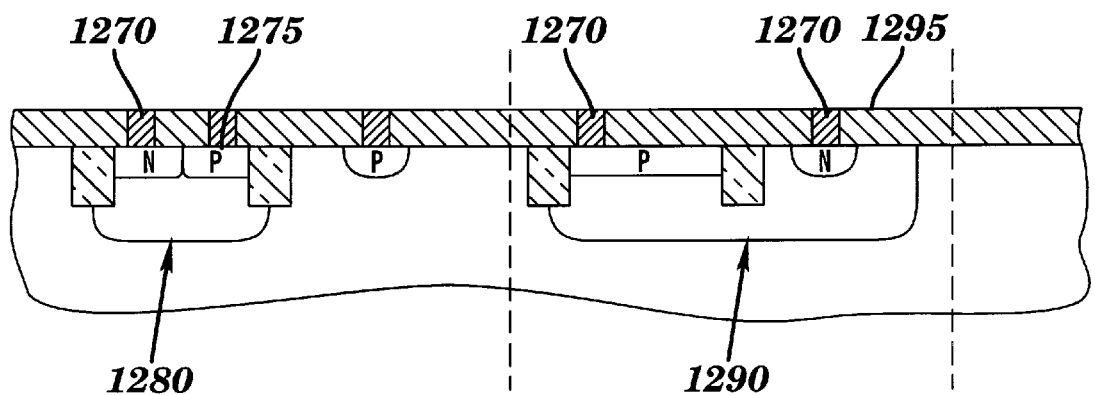

FIGS. 12A through 12E show cross-sectional views illustrating the fabrication of a diode measurement device 1280 and reference device 1290 pair according to the present invention. In FIG. 12A a silicon substrate 1200 has been provided with a p-well 1210 into which dielectric trench isolation 1220 has been formed using techniques known in the art. In FIG. 12B, n-wells 1230 have been formed. In FIG. 12C, the measurement p-diffusion 1240, reference p-diffusion 1250, and the p-well contact diffusion 1250 have been formed by an ion implantation of boron at 10 Kev and at a dose of $10^{15}$ atoms/cm². In FIG. 12D, the diode n-diffusion 1245 and reference n-well contact 1265 have been formed by an ion implantation of arsenic at 25 Kev and at a dose of $10^{15}$ atoms/cm². In FIG. 12E, the diode measurement device 1280 and reference device 1290 pair has been completed through the contact level with stud contacts 1270, silicide layer 1275, and insulative dielectric layer 1295. Alternatively, semi-recessed oxide ("SROX") can be used in place of trench isolation. The process for forming SROX is well known in the art.

Figure 13A:
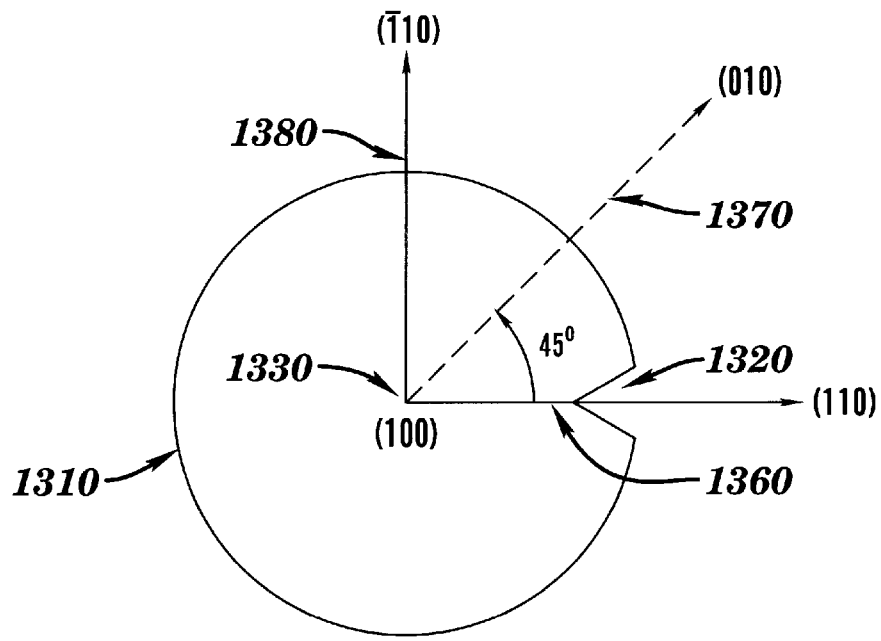
FIGS. 13A through 13C show a plan views of a wafer and the spatial dependence of stress monitoring devices.

Referring now to FIG. 13A, a silicon wafer 1310 is shown. The wafer diameter can be of a typical industry standard, either about 8 inches or 12 inches. The surface of the wafer 1310 defines the (1 0 0) crystal plane or crystal direction. In this example, the (1 0 0) crystal direction is along an axis (not shown) perpendicular to the page. A single notch 1320 is located at the perimeter of the wafer 1310, and is present for manufacturing purposes. This notch 1320 is located on a single radius 1360 from the center point 1330 of the wafer 1310.

Crystal directions are defined with respect to the notch 1320. These crystal directions are (1 1 0) and ($\bar{1}$ 1 0). The (1 1 0) crystal direction is defined by the radius 1360 extending from the wafer's center point 1330 to the notch 1320. The ($\bar{1}$ 1 0) crystal direction is defined by a radius 1380 extending from center point 1330 in a direction rotated 90 degrees from crystal direction (1 1 0) and radius 1360. Similarly, radius 1370, extending from center point 1330 in a direction rotated 45 degrees from crystal direction (1 1 0) and radius 1360, defines crystal direction (0 1 0).

Figure 13B:
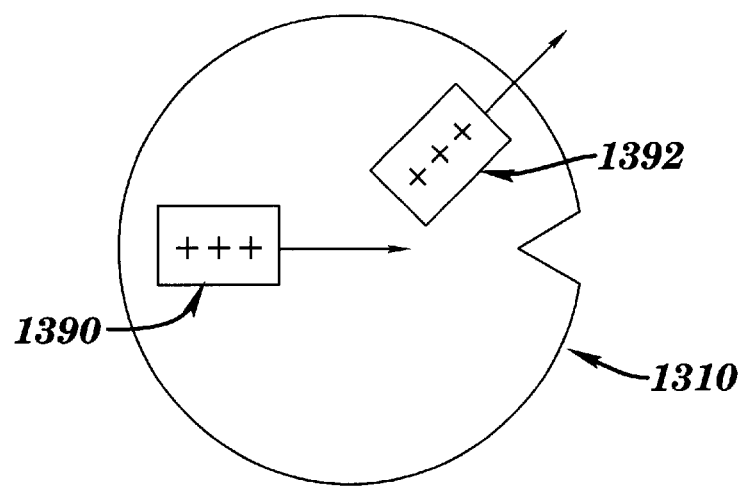

The current conduction properties are equivalent along the (1 1 0) and ($\bar{1}$ 1 0) directions (i.e., radii 1360 and 1380, respectively). However, as is well known from semiconductor solid state physics, the current conduction properties in the plane of the wafer differ along the (0 1 0) direction from those along the (1 0 0) direction (i.e., perpendicular to the paper). Furthermore, the stress couples with the electric field and current perpendicular to the wafer surface, i.e., along the (1 0 0) direction, differently from any in-plane direction. This means that the (σ·δΩ) product (see Equation 1) has a different magnitude for the same physical fabrication process, for the (1 0 0) and (0 1 0) crystal directions in the exponential stress term in previously defined Equation 1, supra, which defines the stress modulated current flow. Thus, it is beneficial to align stress monitoring structures 1390, such as embodied in FIG. 11, so that the diode current flow is along the different crystal directions in a coplanar arrangement. This arrangement is highly advantageous for detecting the differences in current conduction due to stress for devices similarly rotated. Furthermore, as is well known in the art of VLSI device manufacturing, the stress magnitude has a radial dependence, from center-to-edge of the wafer 1310. FIG. 13B shows a pair of stress monitoring structures 1390, 1392 on a wafer 1330. One stress monitoring structure 1390 is oriented along the (1 1 0) crystal direction. The second stress monitoring structure 1392 is oriented along the (0 1 0) crystal direction. The diode current minus the reference current, $(I_m-I_r)$, as discussed supra in the context of FIG. 10, is generally different for any crystal direction for any stress state.

Figure 13C:
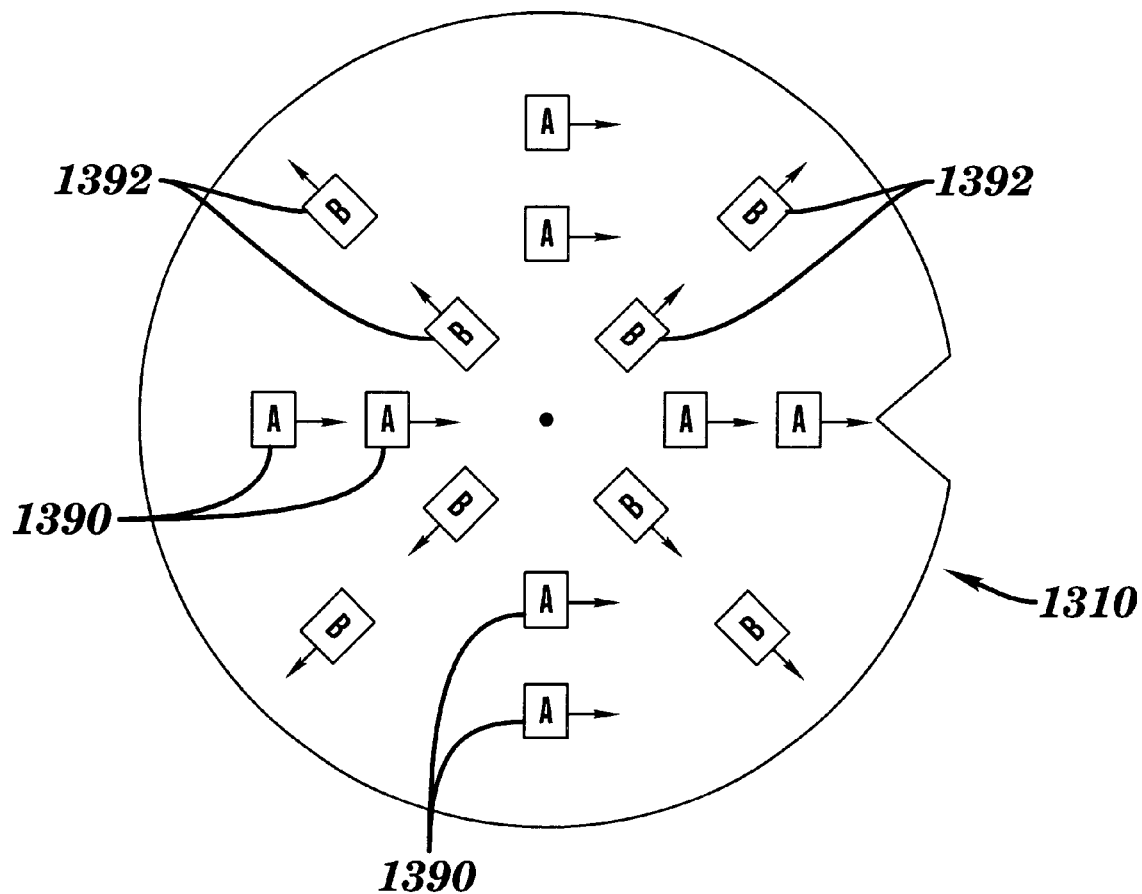

Referring now to FIG. 13C, strategically placing and aligning stress detection structures 1390, 1392 as shown in FIG. 13C, allows sampling of a more complete spatial dependence of stress and diode current conduction on the wafer 1310.

Thus, the stresses exhibit an orientational or rotational dependence with respect to the semiconductor wafer. This information must be considered when placing the measurement and reference devices in the semiconductor wafer under test.

Also, these stress sensors can be embedded on product chips or monitor wafers. If on-chip, then maps of chip-level stress dependence can be determined, which should be related to wafer angular and radial stress dependence.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A stress monitoring set comprising:
   at least one pair of diode devices, said pair comprising a first device and a second device, wherein said first device is a reference device, and said second device is a measurement device wherein each measurement device includes:
      a diode structure formed in a semiconductor material; and
      a non-diode structure including a plurality of isolation trenches surrounding the diode structure.

2. The stress monitoring set of claim 1, wherein each reference device includes:
   a diode structure formed in a semiconductor material; and
   a non-diode structure including a plurality of isolation trenches surrounding the diode structure.

3. The stress monitoring set of claim 1, further comprising a source of electrical current wherein the current is applied to the pairs of diode devices.

4. The stress monitoring set of claim 3, wherein the stress monitoring set further includes a system for translating the amount of stress monitored into standardized data.

5. The stress monitoring set of claim 4, wherein the stress monitoring set is self-contained.

6. A structure for measuring stress in a semiconductor device comprising:
   a pn diode formed on the surface of a semiconductor device, said diode being bounded by a first isolation region having predetermined dimensions;
   a diffusion region formed on the surface of the device, said diffusion region being bounded by a second isolation region having the same dimensions as the first isolation region; and
   contacts formed on said diode and diffusion region for passing current through the diode and through said diffusion region.

7. The structure for measuring stress in a semiconductor device of claim 6, wherein the first isolation region and the second isolation region are filled with dielectric material.

8. The structure for measuring stress in a semiconductor device of claim 6, wherein the first isolation region and the second isolation region are shallow trench isolation regions.

9. The structure for measuring stress in a semiconductor device of claim 6, wherein the first isolation region and the second isolation region are semi-recessed oxide regions.

10. A stress monitoring unit comprising:
    a semiconductor material forming a base structure, said base structure containing a diode structure and a non-diode structure;
    said diode structure formed in the semiconductor material;
    said non-diode structure including a plurality of isolation trenches surrounding the diode structure, said isolation trenches being filled with a dielectric material;
    a system for applying an electrical potential across the diode structure, thereby inducing a diode current to flow through the diode structure;
    a system for measuring the diode current; and
    a system for translating the amount of diode current measured into dimensional units representing the stress on the base structure.

11. The stress monitoring unit of claim 10, wherein the dielectric material is an oxide.

12. The stress monitoring unit of claim 10, wherein the diode structure further comprises a measurement device and a reference device.

13. The stress monitoring unit of claim 12, wherein said measurement device further comprises:
    p-type and n-type diffusions, each of which is surrounded trench isolation in an n-well;
    a p-well surrounding said n-well;
    contacts to the p-type and n-type diffusions, and to the p-well; and
    a parasitic diode located at the junction of the p-type diffusion and the n-well junction.

14. The stress monitoring device of claim 12, wherein the measurement device is formed substantially cross-shaped.

15. The stress monitoring unit of claim 12, wherein said reference device further comprises:
    a p-type diffusion surrounded by a trench isolation in an n-well;
    a p-well surrounding said n-well;
    contacts to the p-type diffusion, and to the p-well; and
    a parasitic diode located at the junction of the p-type diffusion and the n-well junction.

16. The stress monitoring device of claim 15, wherein the reference device is formed substantially cross-shaped.

17. The stress monitoring unit of claim 12, wherein said cross-shaped portions, of said measurement device and said reference device, have substantially identical dimensions.

18. A stress monitoring system for monitoring mechanical stress in a semiconductor substrate containing trench isolation regions comprising:

a semiconductor material forming a base structure, said base structure containing a diode structure and a non-diode structure;

said diode structure formed in the semiconductor material;

said non-diode structure including a plurality of isolation trenches surrounding the diode structure, said isolation trenches being filled with a dielectric material;

a system for applying an electrical potential across the diode structure, thereby inducing a diode current to flow through the diode structure;

a system for measuring the diode current; and a system for translating the amount of diode current measured into dimensional units representing the stress on the base structure.

\* \* \* \* \*